(12) United States Patent
Heise et al.

(10) Patent No.: US 9,360,441 B2
(45) Date of Patent: Jun. 7, 2016

(54) MEASURING HEAD FOR A DEVICE FOR MEASURING THE CONCENTRATION OF AT LEAST ONE GAS IN A GAS SAMPLE

(75) Inventors: Tobias Heise, Lübeck-Travemünde (DE); Alfred Kelm, Badendorf (DE); Hartmut Stark, Stockelsdorf (DE); Günter Steinert, Bad Oldesloe (DE); Peter Dreyer, Pansdsorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 299 days.

(21) Appl. No.: 14/113,647

(22) PCT Filed: Feb. 21, 2012

(86) PCT No.: PCT/EP2012/000755
§ 371 (c)(1),
(2), (4) Date: Oct. 24, 2013

(87) PCT Pub. No.: WO2012/146330
PCT Pub. Date: Nov. 1, 2012

(65) Prior Publication Data
US 2014/0041438 A1    Feb. 13, 2014

(30) Foreign Application Priority Data
Apr. 27, 2011  (DE) .......................... 10 2011 018 670

(51) Int. Cl.
*G01N 25/18*    (2006.01)
*G01N 33/00*    (2006.01)

(52) U.S. Cl.
CPC ............ *G01N 25/18* (2013.01); *G01N 33/0036* (2013.01)

(58) Field of Classification Search
CPC    G01N 25/18; G01N 33/0009; G01N 33/0036
USPC ......................................... 73/25.02; 324/204
See application file for complete search history.

(56) References Cited

U.S. PATENT DOCUMENTS

| | | | | |
|---|---|---|---|---|
| 2,666,893 | A | * | 1/1954 | Munday ................ G01N 27/74 324/201 |
| 2,903,883 | A | * | 9/1959 | Luft ...................... G01N 27/24 73/25.02 |
| 3,866,461 | A | | 2/1975 | Machytka |
| 3,888,110 | A | * | 6/1975 | Clark .................... G01N 30/66 73/23.4 |

(Continued)

FOREIGN PATENT DOCUMENTS

| | | |
|---|---|---|
| CN | 2110874 U | 7/1992 |
| DE | 100 37 380 A1 | 5/2001 |

(Continued)

*Primary Examiner* — Daniel S Larkin
(74) *Attorney, Agent, or Firm* — McGlew and Tuttle, P.C.

(57) ABSTRACT

A measurement head is provided for a device for measuring the concentration of at least one gas, in particular oxygen. A gas sample a measurement element (1) is arranged in the region of an opening on a circuit board (11). To convey gas a duct (16, 17) is formed in each of two metal bodies, which surround the measurement element (1) and serve as magnetic poles. During operation of the measurement head the gas sample flows substantially perpendicularly, first through one of the metal bodies (12, 13), and then through the opening (18) on a side of the measurement element (1) facing the opening and emerges again through the other metal body (14, 15).

20 Claims, 2 Drawing Sheets

(56) References Cited

U.S. PATENT DOCUMENTS

| | | | |
|---|---|---|---|
| 6,430,987 B1 * | 8/2002 | Stark | G01N 27/74 324/204 |
| 6,739,179 B2 * | 5/2004 | Vogel | G01N 27/74 324/201 |
| 6,952,947 B2 * | 10/2005 | Steinert | G01N 27/74 324/204 |
| 2004/0083789 A1 | 5/2004 | Stark et al. | |
| 2011/0252868 A1 | 10/2011 | Doering et al. | |

FOREIGN PATENT DOCUMENTS

| | | |
|---|---|---|
| DE | 102 41 244 C1 | 8/2003 |
| DE | 102 51 130 A1 | 5/2004 |
| DE | 10 2010 014 883 A1 | 10/2011 |

* cited by examiner

MEASURING HEAD FOR A DEVICE FOR MEASURING THE CONCENTRATION OF AT LEAST ONE GAS IN A GAS SAMPLE

CROSS REFERENCE TO RELATED APPLICATIONS

This application is a United States National Phase Application of International Application PCT/EP2012/000755, filed Feb. 21, 2012, and claims the benefit of priority under 35, U.S.C. §119, of German Patent Application DE 10 2011 018 670.0, filed Apr. 27, 2011, the entire contents of which are incorporated herein by reference.

FIELD OF THE INVENTION

The present invention pertains to a measuring head for a device for measuring the concentration of at least one gas in a gas sample.

BACKGROUND OF THE INVENTION

The thermal conductivity of paramagnetic gases is known to change under the effect of magnetic fields. The molecules of a paramagnetic gas have a permanent magnetic torque, which is oriented in an external magnetic field. As a result, there is not only a change in susceptibility and hence an increase in the magnetic flux, but the possibility of transmitting heat energy to adjacent molecules by collisions is also reduced due to the orientation of the molecules. This causes a slight change in the thermal conductivity of the gas. This effect is also manifested in a mixture of paramagnetic and other gases. Since the change in the thermal conductivity of a gas mixture depends on the concentration of a paramagnetic gas contained therein, the percentage, i.e., the concentration of the paramagnetic gas can be inferred by determining the change in the thermal conductivity of the gas mixture. The paramagnetic gases include especially oxygen and nitrogen oxides.

A prior-art device for measuring the concentration of a paramagnetic gas, such as especially oxygen, appears from DE 100 37 380, A1, and is characterized by a modulatable magnetic field source with an air gap, a modulation source for sending a modulation signal to the magnetic field source, a measuring element for sending a measured heat flow signal, which is arranged at least partly within the air gap and is heated to a working temperature by a power source, and by a filter means connected to the measuring element for separating fluctuations from the measured heat flow signal on the basis of the modulation of the magnetic field, wherein the changing amplitude of the fluctuations is an indicator of the percentage of the paramagnetic gas in the gas sample based on the gas-specific change in the thermal conductivity. The measurement of the concentration of the paramagnetic gas, especially oxygen, is carried out in an air gap of the electrically modulatable magnetic system, which air gap is equipped with a measuring gas sample holder. A corresponding measuring gas sample holder is known, for example, from DE 102 51 130, A1. The measuring gas sample holder described there may be arranged, for example, in a measuring head described in DE 102 41 244, C1.

A measuring element is fastened in the prior-art measuring gas sample holder on a bottom plate and a duct plate is cut out for routing the gas in the area of the measuring element and around the measuring element. The measuring gas sample holder is sealed in the upward direction by a cover plate with at least two holes for the gas inlet and gas outlet. The gas is routed in the duct plate in parallel to the bottom plate, on which the essentially planar measuring element is placed. The measuring element is located at a spaced location from the bottom plate by means of spacers and also has a distance from the cover plate. Gas being passed horizontally by the measuring element can diffuse in this manner into the areas above and below the measuring element. Vortices may develop because of pressure fluctuations or rapid changes in the velocity of flow of the gas flowing through the measuring gas sample holder, and these vortices are likewise oriented horizontally, i.e., in parallel to the bottom plate due to the routing of the gas, so that uniform admission of gas to the measuring elements by diffusion is made difficult and the signal may fluctuate. The signal-to-noise ratio is thus impaired.

SUMMARY OF THE INVENTION

A basic object of the present invention is to provide a measuring head improved in respect to the quality of the measured signal for a device for measuring the concentration of at least one gas in a gas sample.

The measuring head according to the present invention for a device for measuring the concentration of at least one gas, especially oxygen, in a gas sample comprises a plate, which carries on one side a measuring element with at least one measurement point for detecting the change in the thermal conductivity of the gas sample and electric lines. Furthermore, a first metal body is arranged above the measuring element and a second metal body is arranged under the second side of the plate under the measuring element, with said metal bodies acting as magnetic poles during the operation of the measuring head. A duct is formed according to the present invention in each metal body for routing the gas and an opening is formed in the plate, so that the gas sample can flow through one of the metal bodies and through the opening on a side of the measuring element facing the opening and can emerge through the other metal body during the operation of the measuring head.

Due to the fact that the gas sample sent to the measuring element first passes through the first metal body located above the measuring element and then through the opening in the plate before the gas again emerges from the second metal body, the direction of the gas flow past the measuring element can be set such that the gas flow takes place essentially perpendicularly to the planar measuring element arranged on the plate. Essentially, perpendicularly is defined here such that the flow vector describing the gas flow may have a slope of between −6° and +6° in relation to the surface normal of the plate at least in the area of the opening in the plate. Vortices, which may develop due to pressure fluctuations or rapid changes in the velocity of flow, are likewise oriented essentially perpendicularly to the surface normal and hence to the measuring element due to this orientation of the gas flow. The signal fluctuations described in the introduction can thus be reduced by this routing of the gas compared to routing the gas horizontally.

The metal bodies may be fastened to the plate, for example, by means of an adhesive. The plate and the metal bodies are connected to one another, in principle, indirectly or directly such that the metal bodies surround the measuring element and at least the part of the plate covered by the measuring element in a gas-tight manner, so that gas can enter the measuring element via the ducts only.

Interfering effects, which may occur due to the flow of gas over the measuring element, can be largely avoided by the measuring element being positioned on the plate relative to the gas routing such that gas will reach the measuring element predominantly by means of diffusion.

The measuring element advantageously partly covers the opening in the plate.

It can be achieved in this manner that the gas flowing through the opening can diffuse to the measuring element and hence to the measurement point even if the second metal body directly adjoins the plate.

Provisions are made in one embodiment of the present invention for the measuring element to comprise a membrane placed on a support frame, and on which membrane the measurement point is arranged, wherein said support frame has a cutout with a reduced height or is interrupted at least on a side facing the opening in the plate.

Due to this design of the support frame, the gas sample can reach the measurement point on the side of the membrane facing the support frame even if the support frame is directly in contact with a surface, especially the plate or the first metal body. Spacers, which are used, for example, in DE 102 51 130, A1, during the assembly of the measuring elements, can therefore be eliminated. The gap width between the magnetic poles is reduced and the magnetic flux density at the measurement point is increased due to the elimination of spacers. This leads to an improvement of the signal-to-noise ratio.

The side of the measuring element carrying the membrane is fastened directly to the plate in an especially preferred embodiment of the present invention, the first metal body adjoins the measuring element on the side of the support frame facing away from the membrane, and the second metal body adjoins the plate.

The word "adjoin" is defined such that the first metal body and the measuring element as well as the second metal body and the plate are directly in contact with one another or at best a small air gap is formed between them, which may develop, for example, due to manufacturing tolerances, for example, especially in case the metal bodies are fastened to the plate by means of an adhesive.

An especially small air gap and thus an especially high flux density of the magnetic field can be obtained in this preferred embodiment, because gas can diffuse on both sides of the membrane to the measurement point even if the first metal body directly touches the measuring element and the second metal body directly touches the plate. Since the measuring element partially covers the opening of the plate, there is a gap having the thickness of the plate between the membrane and the second metal body, and since the support frame has a cutout with a reduced height on the side of the measuring element facing away from the plate or is interrupted, access to the measurement point is also present between the first metal body and the measuring element.

It is advantageous if the first metal body and/or second metal body are assembled from an inner part and an outer part surrounding the inner part at least partially.

The multipart design of the first and/or second metal bodies makes it possible, on the one hand, that the duct formed in the first metal body and/or the duct formed in the second metal body can be advantageously formed by opposite recesses in the respective inner part and outer part. Curved routing of the gas can also be achieved as a result in a precise manner. For example, a gas inlet and/or a gas outlet can be provided as a result laterally on the metal bodies, while coils, by means of which the magnetic field is generated, can be arranged on the sides of the metal bodies facing away from the measuring element.

As an alternative or in addition, the multipart design of the metal bodies makes it possible for the outer part of the first metal body and the outer part of the second metal body to consist advantageously of a non-magnetic material.

As a result, the ferromagnetic inner parts of the metal bodies can be dimensioned such that their extension essentially corresponds to the area of the measuring elements. This has the advantage that the magnetic field is directed essentially towards the measuring element and no current is induced in the ideal case in the electric lines located on the plate, or an induced current is so low that the measured signal is not interfered with or is interfered with only negligibly. The outer parts are designed such that, on the one hand, they receive the inner parts well and in a gas-tight manner and, on the other hand, they can be fastened to the plate readily, for example, by means of an adhesive.

At least two pins advantageously project from at least one side of the plate and the first metal body and/or second metal body each have at least two holes, into which pins projecting on the respective adjoining side of the plate are inserted.

The metal bodies can be positioned highly accurately in this manner relative to the plate and hence relative to the measuring element fastened on the plate. It can be ensured as a result that the gas flow passes through the opening in the plate such that flooding of the measuring element is avoided. Furthermore, the distance between the gas stream passing through the opening and the measuring element can at the same time be made so small that the time that the gas needs to diffuse to the measuring element is so short that changes in the gas concentration can be quickly detected. In particular, the distance is selected to be such that changes in the gas concentration can be detected with a time resolution of less than or equal to 500, msec. At least the metal body over which the gas is fed is to be positioned by means of pins. The metal body located behind the opening in the plate in the direction of flow can be positioned, in principle, with a lower accuracy, so that pins are not absolutely necessary there, but this metal body is preferably positioned by means of at least two pins as well.

It is especially favorable if at least one of the pins is arranged in a hole in the plate such that it projects on both sides of the plate.

The number of pins used to position the two metal bodies can thus be as low as possible.

The measuring head according to the present invention is preferably used in a device for measuring the concentration of at least one gas, especially oxygen, in a gas sample in a medical respiration system.

In particular, the concentration of the oxygen used for the respiration must be able to be determined with a high time resolution and as accurately as possible, i.e., with a good signal-to-noise ratio for the proper operation of respiration systems, for example, anesthesia systems and respiration systems in intensive care. This is made possible by the measuring head, according to the present invention.

The concentration of any paramagnetic gas in a gas sample can be determined, in principle, with the measuring head, according to the present invention.

If two measurement points are arranged on the measuring elements, as this is described in DE 10 2010 014 883,, non-linearities can be compensated, on the one hand, and, on the other hand, the concentration of a gas added to the oxygen can also be determined at the same time. For example, gas mixtures that contain oxygen and helium may be used in long-term respirators in intensive care. Both the concentration of oxygen, and the helium concentration, can be determined by the use of two measurement points with the measuring head, according to the present invention.

The present invention will be explained in more detail below on the basis of an exemplary embodiment shown in the figures. The various features of novelty which characterize the invention are pointed out with particularity in the claims annexed to and forming a part of this disclosure. For a better understanding of the invention, its operating advantages, and specific objects attained by its uses, reference is made to the accompanying drawings and descriptive matter in which preferred embodiments of the invention are illustrated.

DESCRIPTION OF THE PREFERRED EMBODIMENTS

Figure 1:
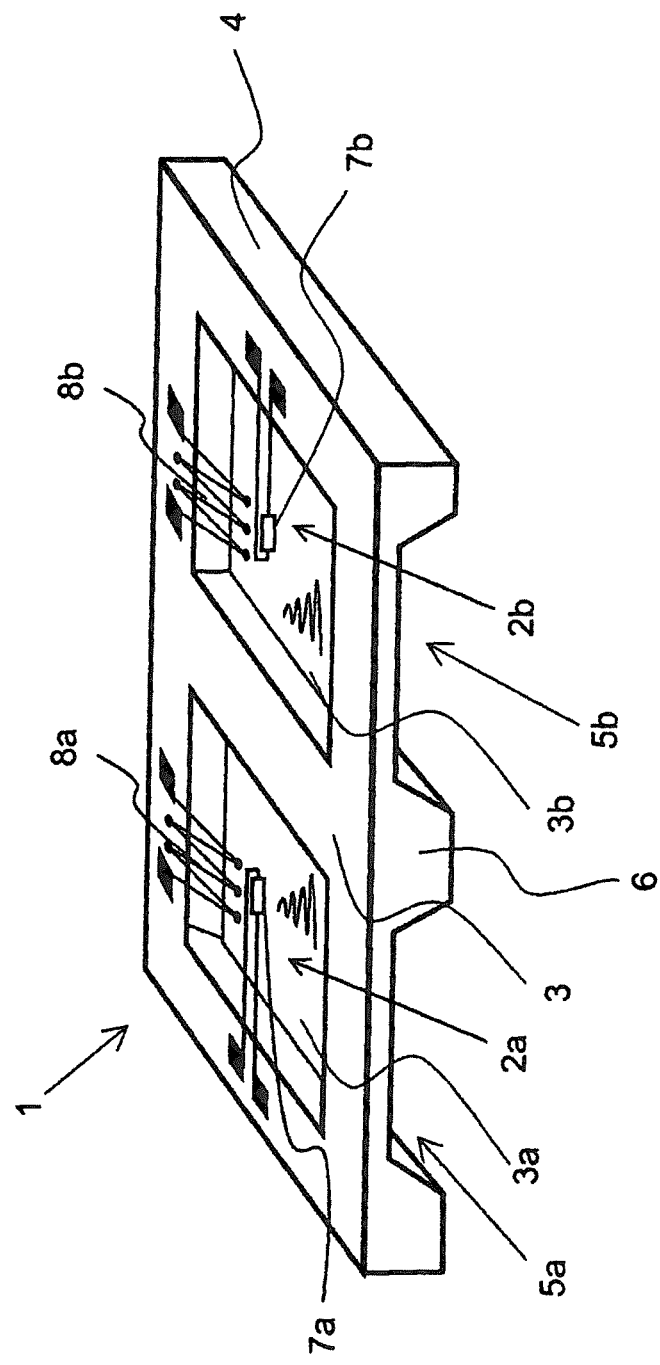
FIG. 1 is a perspective view of a measuring element with two measurement points for use in a measuring head according to the present invention.

Referring to the drawings in particular, identical reference numbers in the Figures designate identical objects.

Figure 2:
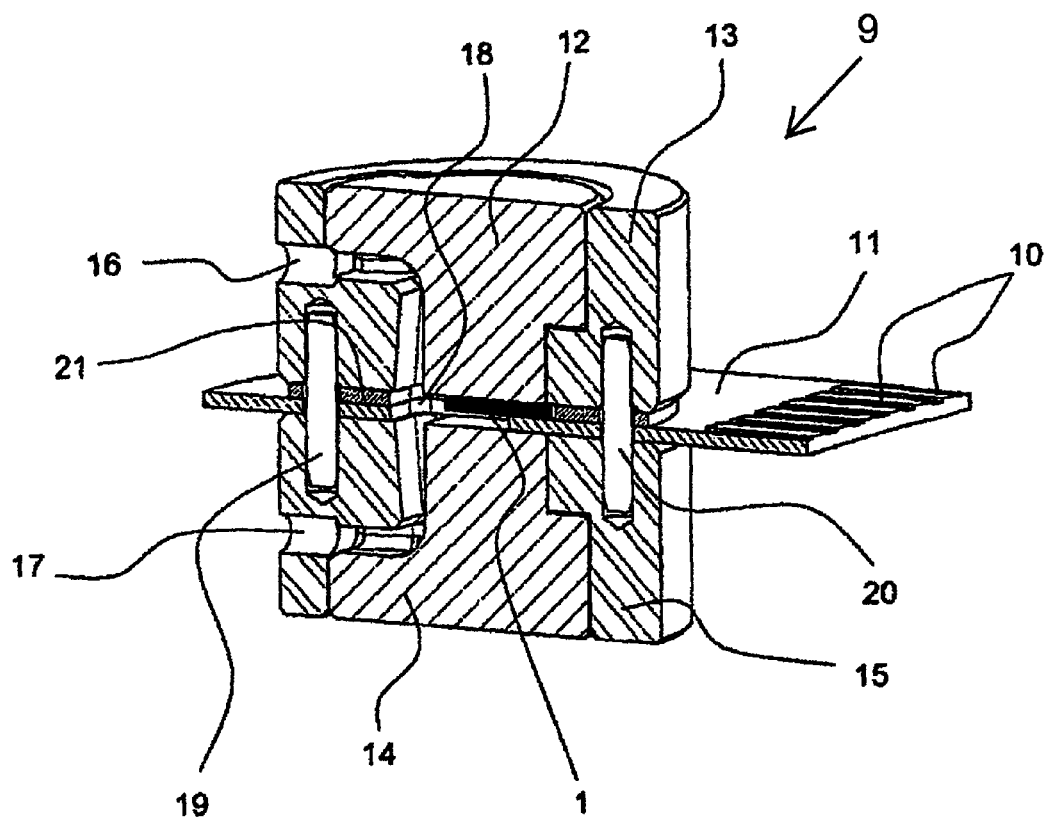
FIG. 2 is a perspective sectional view showing a measuring head according to the present invention with a measuring element according to FIG. 1.

FIG. 1 schematically shows a measuring element 1, which is used in a measuring head 9 shown schematically in FIG. 2. The measuring element 1 comprises a support frame 4, on which an anesthetic-resistant membrane 3, preferably one made of silicon nitride, is arranged. The measuring element 1 has two measurement points 2a, 2b, which are arranged next to each other and which are provided each with a heating means 7a, 7b, and with a heat conduction-measuring unit 8a, 8b. To make possible the entry of the gas sample to be analyzed to both sides of the measurement points 2a, 2b, either the membrane 3a, 3b, can be partially removed, for example, by etching, or the support frame 4 is etched partially to a reduced thickness on one side, hereinafter called the front side, so that it has a reduced height and forms cutouts 5a, 5b, which are separated by a web 6. Entry of gas from the front side is possible through the cutouts 5a, 5b. As an alternative, the support frame 4 may be removed on the front side in the area of the measurement points 2a, 2b, in order to likewise make possible the entry of gas from the front side.

A measuring element of the type being shown in FIG. 1 as well as corresponding measurement methods and measuring devices for measuring the concentration of a gas in a gas sample with such a measuring element are described in DE 10 2010 014 883,, to which reference is explicitly made here (corresponding publication US2011252868, is hereby incorporated by reference in its entirety).

A measuring element with one measurement point or with more than two measurement points may, of course, also be used in the measuring head 9 according to FIG. 2. If only one measurement point is used, this is preferably arranged centrally on the measuring element 1, so that the sides of the support frame 4 that are left in place in case of removal of the support frame 4 in the area of the measurement point have the greatest possible width and are thus especially stable. In case of two and more measurement points, the height is preferably reduced on the front side of the support frame 4, as is shown in FIG. 2 for two measurement points 2a, 2b, so that corresponding cutouts are formed, because when removing, i.e., interrupting the support frame 4, webs similar to web 6 will be left in place on the front side between the measurement points, but these webs are connected to the support frame 4 on a narrow side only and they could therefore break, especially during the mounting of the measuring element 1.

FIG. 2 schematically shows a section through a measuring head 9 for a device for measuring the concentration of at least one gas, especially oxygen, in a gas sample.

Electric lines 10, of which only two were provided with a reference number for clarity's sake, are placed on a circuit board (plate) 11. The measuring element 1 is fastened with the side carrying the membrane 3 on the circuit board 11. The measuring element 1 is arranged such that it partially overlaps an opening 18 formed in the circuit board 11. The front side of the measuring element 1 and hence the cutouts 5a, 5b, point in the direction of opening 18. The measuring element 1 is fastened on the circuit board 11 by contacting the measuring element 1 with the electric lines 10. The electric lines 10 are led for this up into the area of opening 18 and hence into the area of the measuring element 1 arranged there. The course of the electric lines 10 on or in the circuit board 11 is not shown in FIG. 2 for clarity's sake.

A first metal body 12, 13 is arranged adjoining the side of the measuring element 1 facing away from membrane 3. The first metal body 12, 13 comprises an outer part 13 and an inner part 12 arranged in the outer part 13 in a corresponding recess. The inner part 12 is fastened in the outer part 13, for example, by bonding such that no gas can escape or enter via the connection points between the inner part 12 and the outer part 13. A second metal body 14, 15, which is formed from an outer part 15 and an inner part 14 arranged therein in a corresponding recess, is arranged adjoining the underside of the circuit board 11. The inner part 14 is also fastened in the outer part 15, for example, by bonding, such that no gas can escape or enter via the connection points between the inner part 14 and the outer part 15.

A duct 16, which opens from the top side of the circuit board 11 into the opening 18, is formed in the first metal body 12, 13. A duct 17, which opens from the underside of the circuit board 11 into the opening 18, is formed in the second metal body 14, 15. A gas sample can be passed by the measuring element 1 through the ducts 16, 17 essentially perpendicularly through the opening 18. Essentially, perpendicularly means that the gas flows ideally perpendicularly to the surface normal of plate 11 and hence to the surface normal of the planar measuring element 1 fastened thereto. Signal fluctuations, which may develop due to vortices because of pressure fluctuations or rapid changes in the velocity of flow, are largely avoided in this manner, because the vortices are likewise directed perpendicularly to the opening 18 and the measuring element 1. However, deviations by plus or minus 6° from an ideal perpendicular gas stream are permissible. The signal fluctuations are negligible in this case. Moreover, flow relaxation can be achieved by widening the gas stream by a few degrees in the area of the opening. A corresponding widening takes place in the case of the measuring head 9 according to FIG. 2 due to the diameter of the ducts 16, 17 increasing towards the opening 18.

The gas does not flow directly over the measuring element 1, but it reaches, essentially by diffusion, both sides of the membrane 3a, 3b, facing the inner part 12 and the side of said membrane facing the inner part 14, because an air gap, which corresponds essentially to the height of the support frame 4, is formed between the inner part 12 and the membrane 3a, 3b, and gas can diffuse to the measurement points 2a, 2b, through the cutouts 5a, 5b. Furthermore, an air gap, which is determined by the thickness of the circuit board 11, is formed between the side of the measuring element, which said side is placed on the support frame, and the inner part 14. Gas can diffuse in this air gap to the top side of the membrane 3a, 3b.

In the ideal case, the inner part 12 touches the support frame 4 and the inner part 14 touches the underside of the circuit board 11. Due to the fact that the first metal body 12, 13 and the second metal body 14, 15 are connected to the circuit board 12 in a gas-tight manner, for example, by bonding on the respective side facing the circuit board 11, a small air gap can additionally be formed between the measuring element 1 and the inner part 12 as well as the circuit board 11 and the inner part 14 due to the height of the bond. However, this air gap is negligible compared to the thickness of the measuring element 1 and the thickness of the circuit board 11, i.e., the inner part 12 and hence the first metal body 12, 13 adjoins the measuring element 1 in this case as well, while the inner part 14 and hence the second metal body 14, 15 adjoin the circuit board 11.

The air gap between the inner parts 12 and 14 arises essentially from the sum of the thickness of the measuring element 1 and the thickness of the circuit board 11. An especially compact measuring head 9 with the smallest air gap possible between the magnetic poles formed by the first metal body 12, 13 and the second metal body 14, 15 can be manufactured in this manner. Typical thicknesses of the circuit board 11 and measuring elements 1 are on the order of magnitude of 300, m to 400, m, so that an air gap smaller than 1, mm can be obtained.

The ducts 16, 17 have a curved shape in FIG. 2. This is possible, in an especially advantageous manner, due to the fact that the first metal body 12, 13 and the second metal body 14, 15 were manufactured each from an outer part 13, 15 and an inner part 12, 14. A recess each was formed in the inner parts 12, 14 and the outer parts 13, 15, so that the recesses are located opposite each other and form the ducts 16, 17 when the parts are fitted together.

The inner parts 12, 14 are manufactured from a magnetizable metal in the exemplary embodiment according to FIG. 2, so that the inner parts 12, 14 can be magnetized if the measuring head 9 is arranged between two coils and a magnetic field can thus be built up in the area of the measuring element 1. The outer parts 13, 15 are manufactured from a non-magnetizable material. For example, the outer parts 13, 15 are manufactured from aluminum or a ceramic material, such as alumina ($Al_2O_3$). Not only are these materials resistant to anesthetics, but, due to the fact that they are not magnetic, no magnetic field or only a negligible magnetic field is formed between the outer parts 13, 15 during the operation of the measuring head 9. Interfering induction currents in the electric lines 10 are avoided or have a negligible effect on the quality of the measured signal, because the magnetic field is directed predominantly towards the measuring element 1 due to the extension of the inner part 12 and the inner part 14, which extension corresponds essentially to the size of measuring element 1.

Precise positioning of the metal bodies 12, 13 and 14, 15 on the circuit board 11 is guaranteed by pins 19, 20, which are passed through holes in the circuit board 11 and are, for example, pressed and/or bonded permanently in the holes. The first metal body 12, 13 and the second metal body 14, 15 can be localized in this manner so precisely relative to the opening 18 and the measuring element 1 that the gas enters the measurement points $2a,, 2b$, predominantly by diffusion, on the one hand, and, on the other hand, the distance between the side of the measuring element 1 pointing towards opening 18 and the edge of the ducts 16, 17 located in front of the opening 18 is selected to be such that a change in the gas concentration can be detected, for example, with a time resolution of less than or equal to 500, msec.

The gas may, of course, also be routed perpendicularly through the inner part 12 and/or the inner part 14 in a variant, not shown. Since coils are arranged adjoining the inner part 12, 14 and the outer part 13, 15 during the operation for generating the magnetic field, it is necessary in this case to feed and remove the gas through the coils, which can be avoided in the preferred embodiment of the ducts 16, 17 shown in FIG. 2.

The first metal body 12, 13 and the second metal body 14, 15 may, of course, also have a one-part design. The first metal body 12, 13 and the second metal body 14, 15 are manufactured, of course, entirely from a ferromagnetic material in this case. Even though currents are induced, in principle, in the electric lines 10 in this case, these can be compensated basically by forming corresponding conductor loops on the circuit board 11.

To facilitate the mounting of the first metal body 12, 13 on the measuring element 1 and the fastening of the first metal body 12, 13 on the circuit board 11, a spacer 21 made of a non-magnetic material is placed around the measuring element 1 on the circuit board 11. The thickness of the spacer 21 corresponds essentially to the thickness of the measuring element 1, and the contour of the spacer 21 essentially corresponds to the contour of the underside of the outer part 13. As a result, the outer part 13 is flatly in contact with the spacer 21 and the measuring element 1 without being able to tilt after being placed on the pins 19, 20 and can be connected to the spacer 21 and/or to the circuit board 11 at its outer edge, for example, by bonding, in a gas-tight manner. Spacer 21 may be fastened to the circuit board 11, for example, by bonding.

As was already stated above, the measuring head 9 is arranged for operating between two coils for generating a magnetic field, so that the inner parts 12 and 14 are magnetized and a magnetic field is generated in the area of the measurement points $2a,, 2b$. The manner in which the magnetic field generated by the coils can be varied and the manner in which the concentration of a gas, especially of oxygen, in a gas sample can be inferred from the measured signals measured in the measuring element 1 is not the subject of this application and is known to the person skilled in the art. Corresponding devices and methods are known to the person skilled in the art, for example, from DE 100 37 380, A1, as well as DE 10 2010 014 883.

The measuring head 9 shown in FIG. 2 may, of course, also be provided with a measuring element 1 with one measurement point or with more than two measurement points. Furthermore, the measuring head 9 may also be constructed with a larger air gap by, for example, the second metal body 14, 15 directly adjoining the circuit board 11, by the opening 18 being formed in the area of the ducts 16, 17 only, so that the opening does not overlap the measuring element 1, and by the measuring element 1 being fastened with the side of the support frame 4 facing away from the membrane 3 directly on the circuit board 11. To enable gas to also diffuse from the top onto the membrane 3 in this case, the spacer 21 is made, for example, higher by 100 μm to 300 μm than the measuring element 1, so that a corresponding air gap is formed between measuring element 1 and inner part 12. Even though the magnetic flux is reduced between inner part 12 and inner part 14 and the signal-to-noise ratio is consequently impaired in this alternative configuration due to the increased air gap, it may still be sufficient for obtain usable measurement results.

While specific embodiments of the invention have been shown and described in detail to illustrate the application of the principles of the invention, it will be understood that the invention may be embodied otherwise without departing from such principles.

The invention claimed is:

1. A measuring head for a device for measuring the concentration of at least one gas in a gas sample, the measuring head comprising:
a measuring element with at least one measurement point for detecting a change in thermal conductivity of the gas sample;
a plate carrying the measuring element on a first side of the plate;
electric lines connected to the plate and connected to the measuring element;
a first metal body arranged above the measuring element; and
a second metal body arranged under the measuring element under a second side of the plate, wherein the first metal body and the second metal body form magnetic poles during the operation of the measuring head, wherein a duct is formed in each of the first metal body and the second metal body and an opening is formed in the plate for routing the gas, whereby the gas sample can flow through one of the metal bodies and through the opening on a side of the measuring element facing the opening and emerge again through the other metal body during the operation of the measuring head.

2. A measuring head in accordance with claim 1, wherein the measuring element partially covers the opening in the plate.

3. A measuring head in accordance with claim 1, wherein:
the measuring element comprises a membrane on a support frame;
the at least one measurement point is arranged on the membrane;
the support frame has a cutout with a reduced height or an interruption at least on a side facing the opening in the plate.

4. A measuring head in accordance with claim 3, wherein:
the measuring element partially covers the opening in the plate;
the side of the measuring element carrying the membrane is fastened directly to the plate;
the first metal body adjoins the measuring element on a side of the support frame facing away from the membrane; and
the second metal body adjoins the plate.

5. A measuring head in accordance claim 1, wherein at least one of a group comprising the first metal body and the second metal body comprises an inner part and an outer part surrounding the inner part at least partially.

6. A measuring head in accordance with claim 5, wherein the outer part of the first metal body and the outer part of the second metal body consist of a non-magnetic material.

7. A measuring head in accordance with claim 5, wherein the duct formed in the first metal body and/or the duct formed in the second metal body are formed by opposite recesses in the respective inner part and outer part.

8. A measuring head in accordance with claim 1, further comprising at least two pins wherein the first metal body and the second metal body each have at least two holes, into which the at least two pins are inserted.

9. A measuring head in accordance with claim 8, wherein at least one of the pins is arranged in a hole in the plate such that it projects on both sides of the plate.

10. A process for measuring the concentration of a gas, the process comprising the steps of:
providing a measuring head for measuring the concentration of at least one gas, in a gas sample in a medical respiration system, the measuring head comprising:
a measuring element with at least one measurement point for detecting a change in thermal conductivity of the gas sample;
a plate carrying the measuring element on a first side of the plate;
electric lines connected to the plate and connected to the measuring element;
a first metal body arranged above the measuring element; and
a second metal body arranged under the measuring element under a second side of the plate, wherein the first metal body and the second metal body form magnetic poles during the operation of the measuring head, wherein a duct is formed in each of the first metal body and the second metal body and an opening is formed in the plate for routing the gas sample; and
operating the measuring head such that the gas sample flows through one of the metal bodies and through the opening on a side of the measuring element facing the opening and emerges again through the other metal body.

11. A process in accordance with claim 10, wherein the measuring element partially covers the opening in the plate.

12. A process in accordance with claim 10, wherein:
the measuring element comprises a membrane on a support frame;
the at least one measurement point is arranged on the membrane; and
the support frame has a cutout with a reduced height or an interruption at least on a side facing the opening in the plate.

13. A process in accordance with claim 12, wherein:
the measuring element partially covers the opening in the plate;
the side of the measuring element carrying the membrane is fastened directly to the plate;
the first metal body adjoins the measuring element on a side of the support frame facing away from the membrane; and
the second metal body adjoins the plate.

14. A process in accordance with claim 10, wherein at least one of a group comprising the first metal body and the second metal body comprises an inner part and an outer part surrounding the inner part at least partially.

15. A process in accordance with claim 10, wherein an outer part of the first metal body and an outer part of the second metal body consist of a non-magnetic material.

16. A process in accordance with claim 10, wherein the duct formed in the first metal body is formed by opposite recesses in a respective first metal body inner part and first metal body outer part and/or the duct formed in the second metal body is formed by opposite recesses in a respective second metal body inner part and second metal body outer part.

17. A process in accordance with claim 10, further comprising at least two pins wherein the first metal body and the second metal body each have at least two holes, into which the at least two pins are inserted.

18. A process in accordance with claim 17, wherein at least one of the pins is arranged in a hole in the plate such that it projects on both sides of the plate.

19. A measuring head for measuring the concentration of at least one gas in a gas sample, the measuring head comprising:
a measuring element comprising a measurement location for detecting a change in thermal conductivity of the gas sample;

a circuit board carrying the measuring element, the circuit board including electric lines;

a first metal body arranged on a first side of the circuit board, the first metal body defining a first duct; and a second metal body arranged on a second side of the circuit board, the second metal body defining a second duct, the first metal body and the second metal body forming magnetic poles during the operation of the measuring head, the circuit board defining an opening for routing the gas sample, whereby the gas sample flows through the first duct, through the opening and through the second duct.

20. A measuring head in accordance with claim 19, wherein:

the measuring element partially covers the opening in the circuit board;

the measuring element comprises a membrane on a support frame;

the measurement location is on the membrane;

the support frame has a cutout with a reduced height or an interruption at least on a side facing the opening in the circuit board.

\* \* \* \* \*